United States Patent
Glock, Jr.

(10) Patent No.: US 8,528,221 B2
(45) Date of Patent: Sep. 10, 2013

(54) FAMILY HEIGHT RECORDING DEVICE

(76) Inventor: Russell Glock, Jr., Southern Shores, NC (US)

(*) Notice: Subject to any disclaimer, the term of this patent is extended or adjusted under 35 U.S.C. 154(b) by 202 days.

(21) Appl. No.: 13/268,015

(22) Filed: Oct. 7, 2011

(65) Prior Publication Data

US 2012/0096726 A1    Apr. 26, 2012

Related U.S. Application Data

(60) Provisional application No. 61/405,267, filed on Oct. 21, 2010.

(51) Int. Cl.
  *A61B 5/107* (2006.01)
(52) U.S. Cl.
  USPC ............................................. 33/512; 600/587
(58) Field of Classification Search
  USPC ................... 33/486, 487, 488, 512; 600/587
  See application file for complete search history.

(56) References Cited

U.S. PATENT DOCUMENTS

| 1,996,553 | A |   | 4/1935 | Scully |
| 2,216,884 | A |   | 10/1940 | Runge |
| 2,381,428 | A | * | 8/1945 | Attick ............................. 33/512 |
| 4,134,212 | A |   | 1/1979 | Allen |
| 4,495,702 | A |   | 1/1985 | Bergstedt |
| 5,402,585 | A |   | 4/1995 | Lund |
| 7,181,861 | B1 | * | 2/2007 | Leser ............................. 33/512 |
| 2004/0111909 | A1 | * | 6/2004 | Pourmanafzadeh ............ 33/512 |
| 2012/0144686 | A1 | * | 6/2012 | Haykeen ......................... 33/512 |
| 2013/0091718 | A1 | * | 4/2013 | Haykeen ......................... 33/512 |

* cited by examiner

*Primary Examiner* — G. Bradley Bennett
(74) *Attorney, Agent, or Firm* — Daniel Boudwin

(57) ABSTRACT

A height recording device is provided for measuring and recording the growth of multiple individuals over a period of time. The device comprises a recording board, a sliding member and a head rod. The sliding member is slideably secured within a dovetail channel extending vertically along the record board. A spring-loaded bullet catch within the dovetail channel maintains the sliding member static position. A head rod is hingedly secured to the sliding member and may be positioned in a horizontal working position or a vertical storage position. On at least one side of the channel, a graduated measuring means is disposed. Workspace is provided on both lateral sides of the channel so that a user may make written recordings of height measurements, names, dates and other information. The dual workspaces provide users with ample space to make multiple recordings and thus it is ideal for families with multiple children.

12 Claims, 3 Drawing Sheets

FAMILY HEIGHT RECORDING DEVICE

CROSS REFERENCE TO RELATED APPLICATION

This application claims the benefit of U.S. Provisional Application No. 61/405,267 filed on Oct. 21, 2010, entitled "Family Growth Record Board."

BACKGROUND OF THE INVENTION

1. Field of the Invention

The present invention relates to a measuring device for children. More specifically it relates to a height recording board for recording the height of multiple growing individuals over a period of time.

The growth of a child is a special occurrence to many parents and caregivers. Parents often desire to keep track of their child's growth progress over time so that they may see how much the child has grown. Children also enjoy comparing their growth with other members of a family, particularly with other children. Having a record of their children's growth over the years can be an important and valuable keepsake for many parents. In the past, parents would designate an area of a wall for marking children's growth. The children would be placed with their backs against the wall and a marking would be made at the crown of each child's head. Names and dates may be added to keep track of each child's progress. Maintaining growth records in this way can be difficult in today's highly mobile society. Families often move to new homes due to change in employment of the parents, transfer of job position to a new location or simply because the family needs more space. When the family moves, the growth recordings made on a wall are left behind. A portable device is needed that assists a family with maintaining growth records of multiple individuals over a time period, and permits the assembly to be moved from one location to another if required.

2. Description of the Prior Art

The prior art contains a variety of height recording devices for providing visual record of a person's height over time. These devices have familiar design and structural elements for the purposes of recording an individual's growth; however they are not adapted for the task of recording multiple names or notations at a given height location. This is a requirement for extended notes or for those with larger families wherein multiple entries are required to encompass all children on one board. They further do not provide a device that is easily transported from one location to another, which allows a user to retain recorded entries if required to move.

Runge et al, U.S. Pat. No. 2,216,884 discloses a height measurement board for a child comprising a graduated board and a sliding height member. Longitudinal grooves extend on opposing sides of the graduated board member. These longitudinal grooves extend from the top of the board to a lower portion of the same. The slideable height member is secured to the graduated board within the longitudinal grooves and slides upwards and downwards within said grooves. When the height member is not in use it can be slid downward to the bottom of the board where it will lay flat in alignment with the board. The device does not include a separate slideable member secured between the board and the height member. The height member of Runge does not include a magnet that secures the height member in an upright position. Furthermore the graduated portion of Runge extends across the front surface of the graduate board and the device does not have non-graduated side portions, thus making it difficult for a user to record information on the surface of the device. Runge is therefore not suited for the purpose of recordation of a plurality of dates on the surface of the device.

Lund, U.S. Pat. No. 5,402,585 discloses a stadiometer device having an upright rail, a slide member, a height measuring arm, and a scale. The upright rail has a dovetail channel and two side portions disposed on either side of the same. A measuring scale is disposed on both sides of the dovetail channel, the first side having English measurements and the second side having metric measurements. The slide member is movably secured to the dovetail channel such that the slide may move up and down the upright rail. The height measuring arm is secured to the slide by a holder means. This height measurement arm extends outward from the upright rail and contains a transparent portion with a horizontal marking, to allow a user to read the scale through the transparent portion. The height measurement arm is not hinged to fold upwards and be removably retained in that position. The upright rail of Lund does not contemplate side portions that have extraneous area not covered by measuring scales for making written recordings. The device of Lund is suited for use in Doctors offices but not for the purpose of the present invention. Lund does not disclose a side portion having an area that a user can record dates on.

Bergstedt, U.S. Pat. No. 4,495,702 discloses a growth measuring device comprising an elongated measuring stick and a height measuring means that is removably mountable to said elongated stick. The elongated stick consists of a plurality of stick elements that may be removably secured in an end-to-end configuration as needed for measuring the height of a child. The elongated stick member removably secures to a base stand that provides stability to the device while it is in use. An aperture is disposed along an upper portion of said elongated stick for removably securing the height measuring means. The height measuring means has an overall paddle shape and may be removed from the aperture in the elongated stick and moved up and down the same. The height measuring means can be screwed to the elongated stick to temporarily attach it while measurements are being taken. Stickers may be affixed to the sides of the elongated stick to mark the height of a child. There are no extended side portions having an area for a user to write dates and notations on. Additionally the paddle member of Bergstedt does not slide along the elongated stick, but must be removed and repositioned with each use.

Scully et al, U.S. Pat. No. 1,996,553 discloses a device for measuring the height of a child comprising a rigid rod having a scale displayed on a face of the same, a marking means, and a portion for recording. The rigid rod has a groove for slideably connecting with the measuring means. A measuring scale is disposed to one side of the groove and an area is disposed adjoining the measuring scale to allow a user to write in notations and record heights measured. A measuring means is secured to the groove of the rigid rod and consists of a slide and an extending arm hingedly connected thereto. When the device is in use the extendable arm is lowered and the slide is moved vertically within the groove until the extendable arm rests on the crown of a child's head. The extendable arm folds upwards for storage when the device is not in use. Scully does not disclose a centrally disposed dovetail channel for the extendable arm to slide within. The present invention offers writing space on both sides of a central channel making it easy for users to record more than one name at the same height level. Scully does not disclose a device with multiple writing surfaces.

Allen, U.S. Pat. No. 4,134,212 discloses a height measuring device having an elongated panel adapted to be vertically secured to a wall, a vertically slideable head member having lateral flanges, and a head-measuring bar hingedly connected to said head member. The head-measuring bar has a vertical locked state and a horizontal working state. When a person's height is being measured, the head-measuring bar is lowered into its horizontal position and the head member is slid upward until the head-measuring bar is positioned atop a user's crown. A plurality of stickers, markers or pins is provided for placement on the elongated panel to record the height of individuals. The writing space of Allen is centrally disposed on the elongated member; there is no additional writing space on either side of the graduated portion. This lack of space makes it difficult to record multiple entries in one area on the device.

None of the prior art devices disclose writing surfaces disposed on both sides of a centrally positioned measuring means, which is necessary for extended note taking or for recording entries for multiple individuals on the same device. The devices disclosed by the prior art do not address the need for recording multiple names at a given height or providing space for additional information to be recorded thereon. The current invention relates to a device for allowing multiple names or recordings to be made at similar height levels on a height measuring board. It substantially diverges in structural elements from the prior art; consequently it is clear that there is a need in the art for an improvement to the height recording devices. In this regard the instant invention substantially fulfills these needs.

SUMMARY OF THE INVENTION

In view of the foregoing disadvantages inherent in the known types of height recording devices now present in the prior art, the present invention provides a new dual writing surface structure wherein the same can be utilized for providing convenience for the user when making multiple recordings at a similar height level. The device comprises a recording board, a securable sliding member and a head rod. There is a centrally disposed vertical channel in the recording board. The channel comprises a dovetail shape for retaining the dovetail spline secured along the back of the sliding member and within the channel. The sliding member may moved vertically within the channel when the device is in use and secured in position using a spring-loaded bullet catch mechanism. Secured to a lower edge of the sliding member via a vertically hinged joint, there is a head rod. The state of the rod comprises a vertical storage position and a horizontal working position. When the device is not in use the head rod may be folded upwards into the vertical storage position.

A graduated measuring scale is printed on at least one side of the dovetail channel. On both sides of the channel, workspace is provided to allow a user to record names, dates and other notations near a height level. At least one side of the workspace may have horizontal lines printed or scored thereon. The lines provide a guide for handwriting and facilitate neat notation of information. Markers such as stickers may be used on either workspace to mark a specific height level. To measure an individual, the user lowers the head rod into a horizontal position and slides the sliding member downward from the top of the recording board until the head rod touches the crown of the individual's head. The user may then make a note on the workspace of the name of the person being measured, the date and any other pertinent information. When the workspaces are filled up with recordings the device may be coated with a clear coat of sealant to protect the record from aging or damage over time.

It is therefore an object of the present invention to provide a new and improved height recording device having all of the advantages of the prior art and none of their disadvantages.

Another object of the present invention is to provide a new and improved height recording device that provides ample workspace for multiple recordings to be made at a similar height level.

Another object of the present invention is to provide a new and improved height recording device having a foldable head rod for easy storage of the device when it is not in use.

Still another object of the present invention is to provide a new and improved height recording device with a slideable member secured within a dovetail channel, the slideable member being held in a static position by friction created by pressure exerted by a spring-loaded bullet catch mechanism within the channel.

Yet another object of the present invention is to provide a new and improved height recording device having resilient and durable construction.

Other objects, features and advantages of the present invention will become apparent from the following detailed description taken in conjunction with the accompanying drawings.

BRIEF DESCRIPTIONS OF THE DRAWINGS

The above invention will be better understood and the objects set forth above as well as other objects not stated above will become more apparent after a study of the following detailed description thereof. Such description makes use of the annexed drawings wherein like numeral references are utilized throughout.

DETAILED DESCRIPTION OF THE INVENTION

Figure 1:
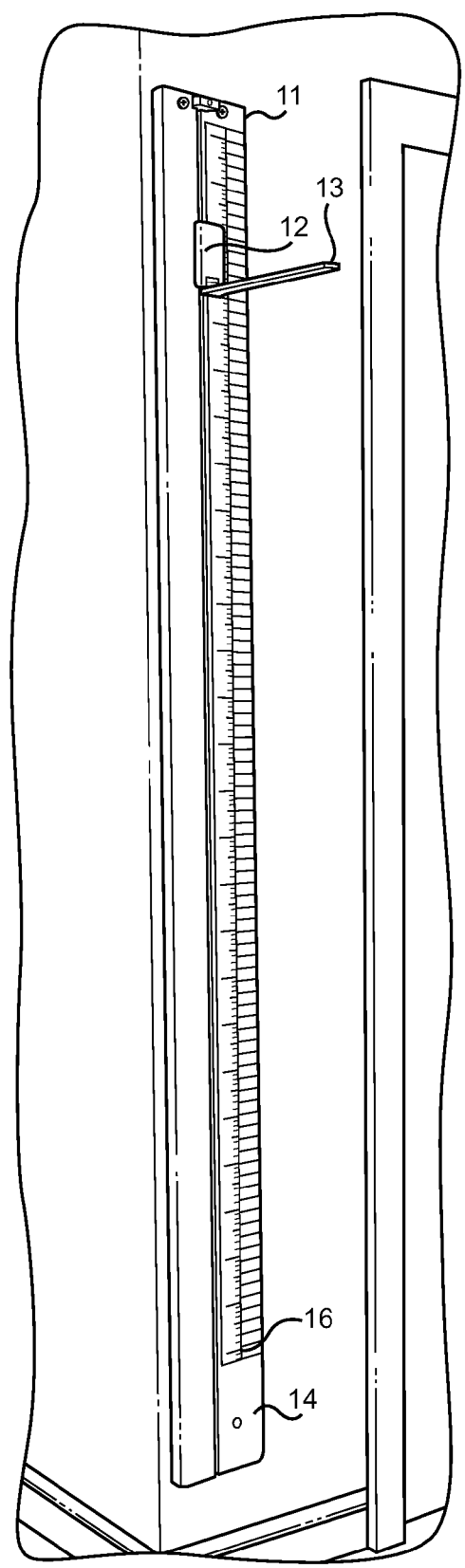
FIG. 1 shows a perspective view of the present height recording device secured to a wall surface.

Reference is made herein to the attached drawings. Like reference numerals are used throughout the drawings to depict like or similar elements of the height recording device. For the purposes of presenting a brief and clear description of the present invention, the preferred embodiment will be discussed as used for assisting a user with recording the height of multiple people. This is for representative purposes only and should not be considered to be limiting in any respect.

Referring now to FIG. 1, there is shown a perspective view of the present height recording device secured vertically to a wall surface. The device comprises a recording board 11, a sliding member 12 and a head rod 13. The record board 11 is adapted for removable mounting to a flat surface. On the front surface of the record board 11, there are disposed two working spaces 14 separated by a dovetail channel extending vertically along the length of the board 11. The channel effectively bisects the front face of the record board. On at least one side of the channel there is printed a graduated measuring means 16. This graduated measuring means 16 measures a person's height as vertical distance from the floor. Careful measurement must be conducted during the securement of the record board to the wall surface to ensure the graduated measuring means accurately reflects the distance from the floor. In an alternative embodiment, there may be no graduated measuring means printed on the record board and an adhesive measuring tape is provided for securing to a side of the channel. The measuring tape can be adjusted or cropped to align its lowest measurement with its distance from the floor surface.

Figure 2:
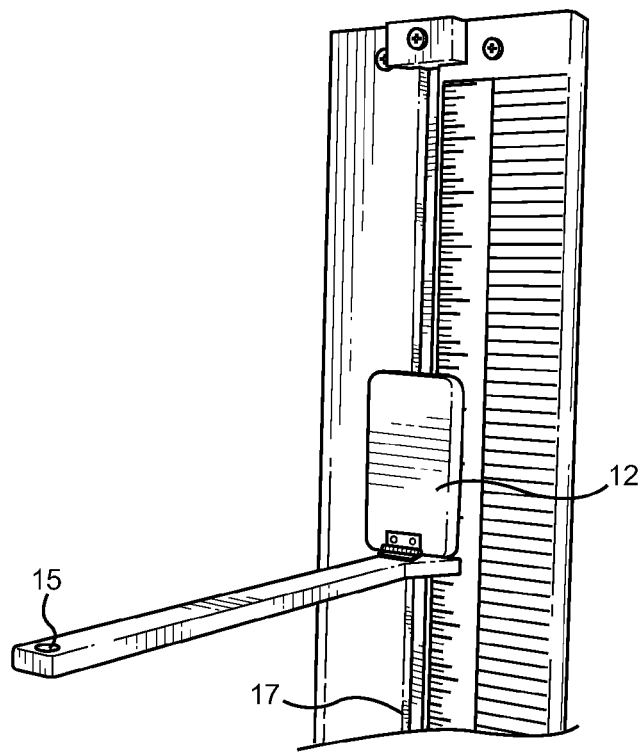
FIG. 2 shows a perspective view of the present height recording device with the head rod extended in a horizontal position.

Referring now to FIG. 2, there is shown a close-up perspective view of the present height recording device wherein the head rod 13 is extended. The head rod 13 is hingedly secured to a lower edge of the sliding member 12. The head rod 13 has an extended horizontal position that may be used for measuring a person's height. The head rod may also be folded into a vertical position for stowage. A magnet 15 is disposed at the distal end of the head rod along its upper surface. When the rod 13 is folded into a vertical position, the magnet 15 removably secures the rod 13 to a ferric object disposed along the upper edge of the record board 11, such as a screw, nail, or similar metal insert. In this way, the rod 13 and sliding member 12 are secured in position at the top of the board 11 when not in use, reducing the chances of these items being snagged by passersby or other objects. In an alternative embodiment, the magnet 15 may be disposed at the proximal end of the head rod. A metal object such as a screw or insert is disposed along the sliding member 12 such that when the head rod 13 is folded upwards, the magnet 15 engages with the metal object on the sliding member 12 and the two may be slid along the board 11 in a stowed configuration.

A dovetail spline is secured to the back of the sliding member 12. The sliding member 12 is slideably secured within a dovetail channel 17 provided along the length of the board via the dovetail spline inserted therein. A catch is provided to prevent the sliding member from sliding down the channel or otherwise moving if released. The catch may comprises a button catch, spring compression fitting or any other means for providing sufficient contact pressure on the record board such that the sliding member is retained at a specified height. The sliding member may be moved vertically within the channel by a user and then placed in a storage position by folding the hingedly secured head rod 13 upward such that the magnetic securing means disposed thereon interfaces with a metal object near the upper edge of the record board 11. The sliding member 12 may have any desired geometrical or decorative shape. The head rod 13 may similarly have any basic geometric or decorative shape.

Figure 3:
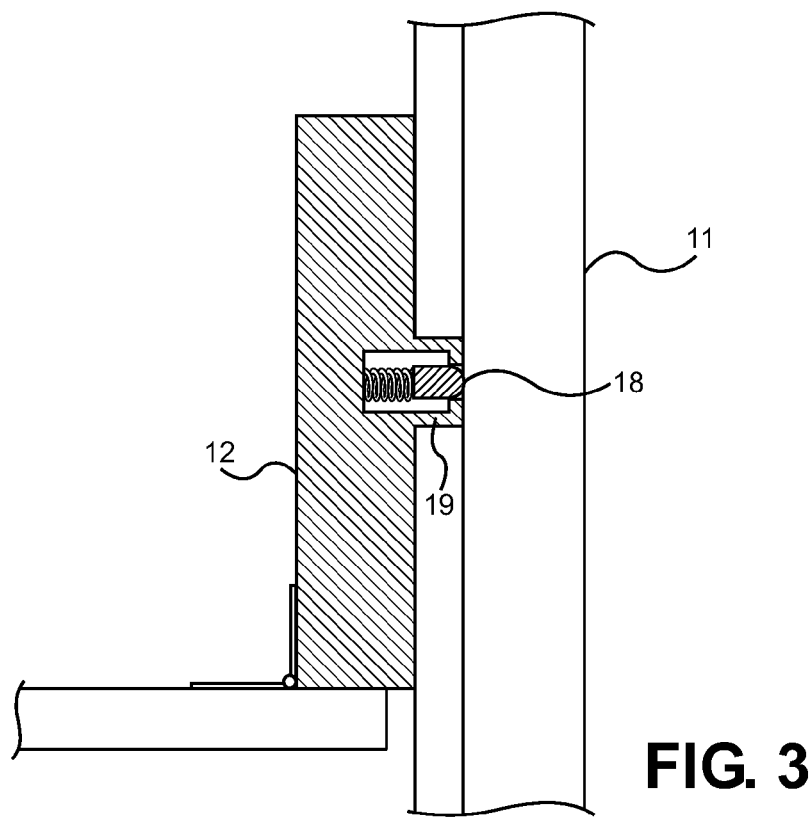
FIG. 3 shows a cross-section view of the present height recording device with the head rod extended in a horizontal position.

Referring now to FIG. 3 there is shown a cross-section view of the present height recording device. The sliding member 12 is secured within the dovetail channel via the dovetail spline 19, which incorporates a catch means for maintaining its position along the channel while in use or while stowed. The catch means comprises a spring-loaded button catch 18 that prevents the sliding member 12 from moving up or down the board unless desired by a user, whereby the bullet catch 18 exerts a load on the interior of the channel to apply pressure on the spline. The pressure against the channel creates sufficient friction to prevent relative movement, until a user forcibly slides the sliding member 12 by hand to overcome the friction.

Figure 4:
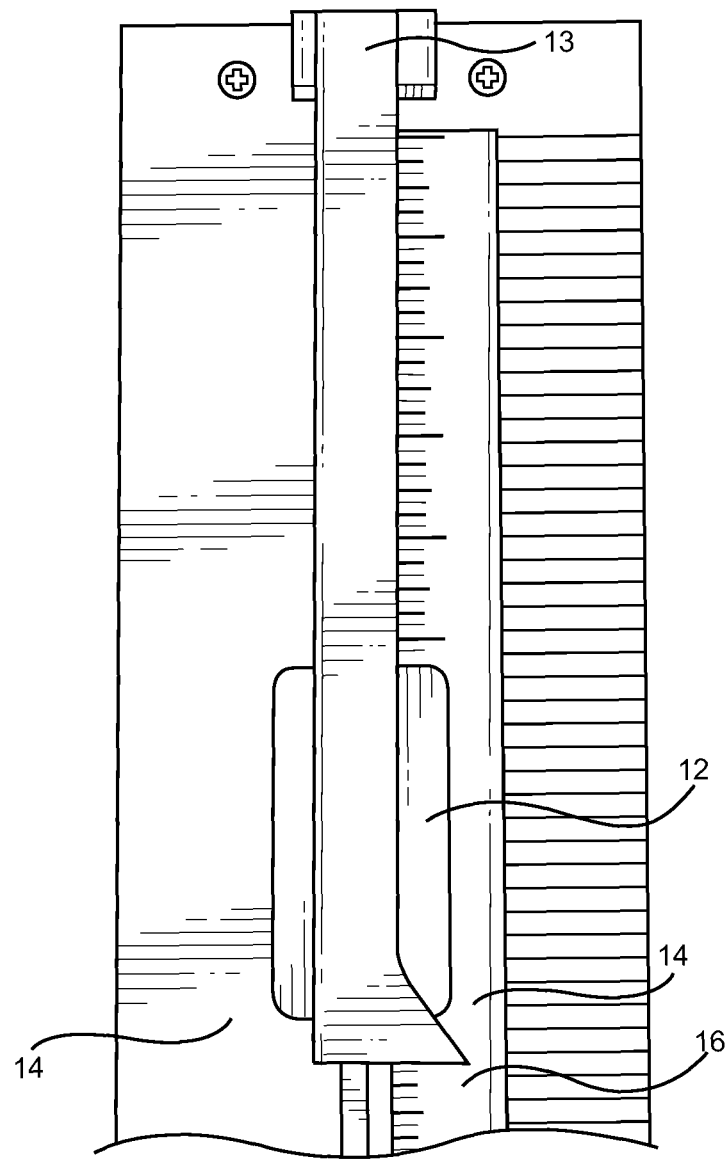
FIG. 4 shows a front view of the present height recording device with the head rod folded into a vertical position.

Referring now to FIG. 4, there is shown a frontal view of the present height recording device. The head rod 13 and sliding member 12 are placed in a vertical storage position near the upper edge of the record board 11. The graduated measuring means 16 is disposed on one side of the record board and two workspaces 14 are disposed on opposing sides of the same. These workspaces 14 provide space for users to make written recordings about a measured height. Information such as the name, date and age of the person being measured may be written in either workspace. Families with multiple children may have children of approximately the same height and will find the dual workspaces 14 convenient for recording information about both children. Workspaces may also be designated for different members of the family so that comparisons may easily be made. One workspace 14 may be reserved for a first child and the other workspace reserved for a second child. Additionally one workspace may be reserved for adults, while the other workspace is for children. In this manner children may note their growth progress and compare it with other members of the family. In a preferred embodiment, at least one workspace has horizontal lines for providing a writing guide that facilitates neat and organized written recordings. In an alternative embodiment, there may be no lines printed on the workspaces; however an adhesive sheet having horizontal lines printed thereon may be used to secure organized remarks onto a workspace if so desired. Once the available spaces have been filled with recordings, the device may be coated with a clear sealant to preserve the recordings over an extended period of time without risk of damage or fading.

In use, a child stands with their back against the record board with their hands by their sides. The user then removes the sliding member from the storage position above the child and folds the head rod downward until it is horizontal. The sliding member is then moved vertically downward within the dovetail channel until the head rod rests against the crown of the child's head. Pressure exerted by the button catch on the sliding member will keep the head rod in place. A user may then make a visual comparison between the head rod and a corresponding height on the graduated measuring means. The height is recorded on one of the workspaces along with any pertinent information, notes, drawings, or stickers that a user may wish to add. The user then slides the sliding member back towards the upper portion of the record board, folds the head rod upwards into a vertical position and engages the magnetic securing means.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim the following:
1. A height-measuring device, comprising:
   a record board having a dovetail channel centrally disposed along and extending vertically along its front face;
   a first workspace disposed on a first side of said dovetail channel;
   a second workspace disposed on a second side of said dovetail channel;
   a graduated measuring means disposed along a side of said dovetail channel;
   a sliding member slideably secured within said dovetail channel;
   a button catch disposed within a recess on the rear of said sliding member and capable of exerting sufficient pres- sure to retain said sliding member at a height position within said dovetail channel;

a head rod hingedly secured to a lower edge of said sliding member.

2. The device of claim 1, wherein at least one of either said first or second workspace further comprises horizontal lines printed thereon for providing writing guidelines.

3. The device of claim 1, further comprising an adhesive sheet adapted to fit over a first or second workspace and having horizontal lines printed thereon for providing writing guidelines.

4. The device of claim 1, further comprising a second graduated measuring means disposed along a side of said dovetail channel opposing said first graduated measuring means.

5. The device of claim 1, wherein a magnet is disposed along a distal end and upper surface of said head rod, such that said magnet removably secures said head rod in a vertical position to a metal object disposed along an upper edge of said record board.

6. The device of claim 1, wherein a magnet is disposed along a proximal end and upper surface of said head rod, such that said magnet removably secures said head rod in a vertical position to a metal object disposed along an upper edge of said sliding member.

7. A height-measuring device, comprising:
a record board having a dovetail channel centrally disposed along and extending vertically along its front face;
a first workspace disposed on a first side of said dovetail channel;
a second workspace disposed on a second side of said dovetail channel;
an adhesive sheet having a graduated measuring means printed thereon, adapted for placement on a side of said dovetail channel;
a sliding member slideably secured within said dovetail channel;
a button catch disposed within a recess on the rear of said sliding member and capable of exerting sufficient pressure to retain said sliding member at a height position within said dovetail channel;
a head rod hingedly secured to a lower edge of said sliding member.

8. The device of claim 7, wherein at least one of either said first or second workspace further comprises horizontal lines printed thereon for providing writing guidelines.

9. The device of claim 7, further comprising an adhesive sheet adapted to fit over a first or second workspace and having horizontal lines printed thereon for providing writing guidelines.

10. The device of claim 7, further comprising a second graduated measuring means disposed along a side of said dovetail channel opposing said first graduated measuring means.

11. The device of claim 7, wherein a magnet is disposed along a distal end and upper surface of said head rod, such that said magnet removably secures said head rod in a vertical position to a metal object disposed along an upper edge of said record board.

12. The device of claim 7, wherein a magnet is disposed along a proximal end and upper surface of said head rod, such that said magnet removably secures said head rod in a vertical position to a metal object disposed along an upper edge of said sliding member.

\* \* \* \* \*